(12) United States Patent
Mayrhofer

(10) Patent No.: US 9,644,211 B2
(45) Date of Patent: May 9, 2017

(54) PLASMID FOR MINICIRCLE PRODUCTION

(71) Applicant: Peter Mayrhofer, Vienna (AT)

(72) Inventor: Peter Mayrhofer, Vienna (AT)

(*) Notice: Subject to any disclaimer, the term of this patent is extended or adjusted under 35 U.S.C. 154(b) by 0 days.

(21) Appl. No.: 14/785,369

(22) PCT Filed: Apr. 11, 2014

(86) PCT No.: PCT/EP2014/057444
§ 371 (c)(1),
(2) Date: Oct. 19, 2015

(87) PCT Pub. No.: WO2014/170238
PCT Pub. Date: Oct. 23, 2014

(65) Prior Publication Data
US 2016/0076042 A1 Mar. 17, 2016

(30) Foreign Application Priority Data
Apr. 19, 2013 (GB) .................................. 1307075.0

(51) Int. Cl.
| | | |
|---|---|---|
| C12N 15/00 | (2006.01) | |
| C07H 21/02 | (2006.01) | |
| C12N 15/64 | (2006.01) | |
| C12N 15/74 | (2006.01) | |
| A61K 48/00 | (2006.01) | |

(52) U.S. Cl.
CPC .......... *C12N 15/64* (2013.01); *A61K 48/0058* (2013.01); *C12N 15/74* (2013.01)

(58) Field of Classification Search
None
See application file for complete search history.

(56) References Cited

U.S. PATENT DOCUMENTS

| 2013/0034882 A1 | 2/2013 | Chen et al. |
| 2013/0203121 A1 | 8/2013 | Rehberger et al. |
| 2016/0076042 A1* | 3/2016 | Mayrhofer ............. C12N 15/64 514/44 R |

FOREIGN PATENT DOCUMENTS

| WO | WO 02/083889 A2 | 10/2002 |
| WO | WO 2004/020605 A2 | 3/2004 |
| WO | WO 2010/002470 A1 | 1/2010 |
| WO | WO 2012/045722 A1 | 4/2012 |

OTHER PUBLICATIONS

Bigger et al., "An araC-controlled bacterial cre expression system to produce DNA minicircle vectors for nuclear and mitochondrial gene therapy," *J. Biol. Chem.*, 276(25): 23018-23027 (2001).

Chabot et al., "Minicircle DNA electrotransfer for efficient tissue-targeted gene delivery," *Gene Therapy*, 20(1): 62-68 (2013).
Chen et al., "Determination of the optimal aligned spacing between the Shine-Dalgarno sequence and the translation initiation codon of *Escherichia coli* mRNAs," *Nucleic Acids Res.*, 22(23): 4953-4957 (1994).
Chen et al., "Improved production and purification of minicircle DNA vector free of plasmid bacterial sequences and capable of persistent transgene expression in vivo," *Hum. Gene Ther.*, 16(1): 126-131 (2005).
Chen et al., "Minicircle DNA vectors devoid of bacterial DNA result in persistent and high-level transgene expression in vivo," *Mol. Ther.*, 8(3): 495-500 (2003).
Cranenburgh et al., "*Escherichia coli* strains that allow antibiotic-free plasmid selection and maintenance by repressor titration," *Nucleic Acids Res.*, 29(5): E26 (2001).
Darquet et al., "A new DNA vehicle for nonviral gene delivery: supercoiled minicircle," *Gene Ther.*. 4(12): 1341-1349 (1997).
Jechlinger et al., "Minicircle DNA immobilized in bacterial ghosts: in vivo production of safe non-viral DNA delivery vehicles," *J. Mol. Microbiol. Biotechnol.*, 8(4): 222-231 (2004).
Jechlinger, W., "Optimization and delivery of plasmid DNA for vaccination," *Expert Rev. Vaccines*, 5(6): 803-825 (2006).
Jia et al., "A Nonviral Minicircle Vector for Deriving Human iPS Cells," *Nature Methods*, 7(3): 197-199 (2010).
Kay et al., "A robust system for production of minicircle DNA vectors," *Nature Biotechnology*, 28(12): 1287-1289 (2010).
Kobelt et al. "Performance of High Quality Minicircle DNA for In Vitro and In Vivo Gene Transfer," *Molecular Biology: Part B of Applied Biochemistry and Biotechnology*, 53(1): 80-89 (2012).
Mairhofer et al., "A novel antibiotic free plasmid selection system: advances in safe and efficient DNA therapy," *Biotechnol. J.*, 3(1): 83-89 (2008).
Mayrhofer et al., "Minicircle-DNA production by site specific recombination and protein-DNA interaction chromatography," *J. Gene Med.*, 10(11): 1253-1269 (2008).
Ringquist et al., "Translation initiation in *Escherichia coli*: sequences within the ribosome-binding site," *Mol. Microbiol.*, 6(9): 1219-1229 (1992).
Sadler et al., "A perfectly symmetric lac operator binds the lac repressor very tightly," *Proc. Natl. Acad. Sci. USA*, 80(22): 6785-6789 (1983).
Schurr et al., "Identification and characterization of *E.coli* ribosomal binding sites by free energy computation," *Nucleic Acids Res.*, 21(17): 4019-4023 (1993).
European Patent Office, International Search Report in International Application No. PCT/EP2014/057444 (Jun. 30, 2014).
European Patent Office, Written Opinion in International Application No. PCT/EP2014/057444 (Jun. 30, 2014).
Intellectual Property Office, Combined Search and Examination Report in Great Britain Patent Application No. 1307075.0 (Oct. 21, 2013).

* cited by examiner

*Primary Examiner* — Michael Burkhart
(74) *Attorney, Agent, or Firm* — Leydig, Voit & Mayer, Ltd.

(57) ABSTRACT

The present invention relates to a plasmid for minicircle production, a method for providing a minicircle and a minicircle produced by said method as well as a pharmaceutical composition comprising the same.

16 Claims, 4 Drawing Sheets

PLASMID FOR MINICIRCLE PRODUCTION

CROSS-REFERENCE TO RELATED APPLICATIONS

This patent application is the U.S. national phase of International Application No. PCT/EP2014/057444, filed on Apr. 11, 2014, which claims the benefit of Great Britain Patent Application No. 1307075.0, filed Apr. 19, 2013, the disclosures of which are incorporated herein by reference in their entireties.

TECHNICAL FIELD

The present invention relates to a plasmid for minicircle production, a method for providing a minicircle and a minicircle produced by said method as well as a pharmaceutical composition comprising the same.

BACKGROUND OF THE INVENTION

The application of efficient non-viral gene transfer systems is desirable in modern DNA-vaccine design and gene therapy protocols. Therefore, many administration modes and formulations are under investigation to ensure optimal delivery of plasmid DNA for gene transfer. A significant improvement in the application of plasmid based DNA molecules in this field is the use of so-called minicircle-DNA.

Conventional plasmid vectors include a bacterial backbone and a transcription unit. The transcription unit carries the target gene or sequence (e.g. a sequence coding for a therapeutically useful protein) along with necessary regulatory elements needed for a specific gene transfer application. [1] The bacterial backbone unit includes inter alia elements which are needed for the stable propagation of plasmid-DNA in bacterial cells. [1] The latter elements, i.e. an antibiotic resistance gene as well as a bacterial replication origins but also unmethylated CpG motives or cryptic expression signals are clearly undesired for clinical applications of DNA-molecules in humans.

To remove these unwanted elements without destroying the supercoiled structure of the transcription unit, the minicircle technology has been developed [2-5]. This technology creates a minimal expression cassette by an in vivo site-specific recombination process which removes all unwanted backbone elements. In the course of this process, a so-called parental plasmid is divided by a recombinase into a miniplasmid carrying the backbone sequences and a minicircle consisting of almost exclusively the desired expression cassette (minimal expression cassette).

Following the site-specific recombination process the resulting mixture of plasmid species (i.e. minicircles, miniplasmides and to some extend unrecombined parental plasmid) must be separated, to isolate the desired minicircle-DNA. Different strategies have been developed for this purpose, including affinity based chromatographic purification and in vivo restriction. A successful approach to affinity based chromatographic purification has been described by Mayrhofer et al. [6]. Another method for minicircle purification, i.e. the in vivo restriction approach has been described by Chen et al. and Kay et al. [7, 8].

Chen and coworkers developed a technique to degrade the miniplasmid and remaining (unrecombined) parental plasmid in vivo via co-expression of a restriction enzyme [7]. The homing endonuclease used in this approach (I-SceI) and the PhiC31 integrase (i.e. the recombinase) are both located on the parental plasmid. Both genes are under the control of a $P_{BAD}$/araC arabinose promoter. Thus, addition of the inducer L-arabinose results in the simultaneous expression of both the integrase and the endonuclease. However, when using this approach, even after 240 minutes of co-expression of integrase and endonuclease, contaminating miniplasmids and parental plasmids still make up about 3% of the total plasmid DNA [7]. In addition to that, the simultaneous expression of both the endonuclease and the integrase leads to undesired early degradation of the parental plasmid, thus reducing the minicircle yield obtained by said process. Various measures, including change of pH and temperature of the culture broth during the production process, were necessary to minimize premature degradation of the parental plasmid [7].

Another in vivo restriction approach described by Kay et al. [8] uses a bacterial producer strain expressing both the PhiC31 integrase (i.e. the recombinase) and a I-SceI homing endonuclease, whereby multiple copies of both enzymes which are under the control of the inducible promoter system $P_{BAD}$/araC too, have been integrated into the chromosome of said producer strain. Although for this system fewer contaminations of about 1.5% are reported (compared to up to 15% with the system described by Chen et al. [7] as stated in [8]), it also requires change of both pH-value and temperature in the culture broth during production, thus making a large scale production process difficult. Furthermore, as bacteria tend to lose redundant, unnecessary genomic information, stability problems of the producer strain may occur.

Hence, there remains a need for methods for the production of minicircles achieving high yields of minicircles, allowing for an efficient isolation of the minicircles produced and being suitable for large scale production.

OBJECT AND SUMMARY OF THE INVENTION

Hence, it is an object of the present invention to provide a parental plasmid as well as a method for the production of minicircles addressing the above-mentioned needs.

In one aspect the present invention relates to a plasmid comprising the following units:
- an endonuclease restriction site,
- a promotorless endonuclease expression cassette,
- a promoter,
- a sequence coding for an enzyme that catalyzes site-specific recombination,
- at least two recognition sequences for the enzyme that catalyzes site-specific recombination, and
- a sequence of interest and an element preventing expression of the endonuclease which are both arranged between said recognition sequences, wherein the functional units are arranged on the plasmid such that the endonuclease expression cassette is placed under control of the promoter only after recombination at the specific recognition sequences.

One embodiment relates to the plasmid described herein, wherein upon expression of the sequence coding for the enzyme that catalyzes site-specific recombination the plasmid is divided into a minicircle comprising the sequence of interest and the element preventing expression of the endonuclease and a miniplasmid comprising the endonuclease restriction site, the endonuclease expression cassette, the promoter and the sequence coding for an enzyme that catalyzes site-specific recombination.

In another embodiment of the plasmid described herein, the endonuclease restriction site is present on the miniplasmid after recombination.

In a further embodiment of the plasmid described herein, the endonuclease is selected from the group consisting of I-TevI, I-CreI, I-DmoI, I-PpoI, I-SceI and/or I-SceII.

In a further embodiment of the plasmid described herein, the plasmid further comprises at least one identification sequence, optionally a miniplasmid identification sequence.

In yet another embodiment of the plasmid described herein, the identification sequence is a sequence which is capable to specifically bind to a protein in order to form a stable DNA-protein complex, optionally a lac operator site which specifically binds to a LacI repressor protein.

Another embodiment relates to the plasmid described herein, wherein the enzyme that catalyzes site-specific recombination is selected from the group consisting of ParA resolvase of plasmid RK2 or RP4, φλ integrase, φCh31 integrase, γδ resolvase, Hin recombinase, φP1 Cre, yeast 2 micron Flp, Tn3 resolvase, Tn21 resolvase and/or XerCD, optionally the enzyme that catalyzes site-specific recombination is the Par A resolvase of plasmid RK2 or RP4.

In one embodiment of the plasmid described herein, the recognition sequences for the enzyme that catalyzes site-specific recombination are selected from the group consisting of ParA resolution sites (res-sites), attB and attP for φλ integrase or φCh31 integrase, γδ res sites, hixL, hixR, lox sites, FRT sites, Tn3 res sites, Tn21 res sites and/or cer sites. For example, the recognition sequences are ParA resolution sites (res-sites).

In a further embodiment of the plasmid described herein, the promoter is independently selected from the group consisting of a constitutive promoter and a positively and/or negatively regulated promoter.

Yet another embodiment of the plasmid described herein relates to the plasmid, wherein the element that prevents expression of the endonuclease is an operator and/or a transcription terminator, e.g. a transcription terminator.

In another embodiment of the plasmid described herein, the plasmid comprises at least two elements that prevent expression of the endonuclease.

A further embodiment relates to a plasmid described herein, wherein the sequence of interest is a sequence coding for a product of therapeutic value.

Another aspect of the present invention relates to a method for providing a minicircle, comprising the following steps:
a) transfecting a plasmid as described herein into an organism capable to replicate said plasmid,
b) recombinating at the recognition sequences for the enzyme that catalyzes site-specific recombination in order to obtain a minicircle comprising the sequence of interest and the element that prevents expression of the recombinase and a miniplasmid comprising the endonuclease restriction site, the endonuclease expression cassette, the promoter and the gene coding for an enzyme that catalyzes site-specific recombination,
c) purifying the minicircle.

In one embodiment of the method described herein, between steps b) and c) restricting the miniplasmid by means of the endonuclease is performed.

In another embodiment of the method described herein, in step c) the non-recombined plasmid and/or the miniplasmid is/are immobilized on a solid support, e.g. on a chromatography column.

In a further embodiment of the method described herein, immobilizing is performed by means of a miniplasmid identification sequence, wherein the miniplasmid identification sequence is capable of specifically binding to a protein in order to form a stable DNA-protein complex, optionally a lac operator site which specifically binds to a LacI repressor protein.

A further aspect of the present invention relates to a minicircle provided by the method as described herein.

Yet another aspect of the present invention relates to a pharmaceutical composition comprising a minicircle described herein and at least one pharmaceutically acceptable excipient.

DETAILED DESCRIPTION OF THE INVENTION

Figure 1:
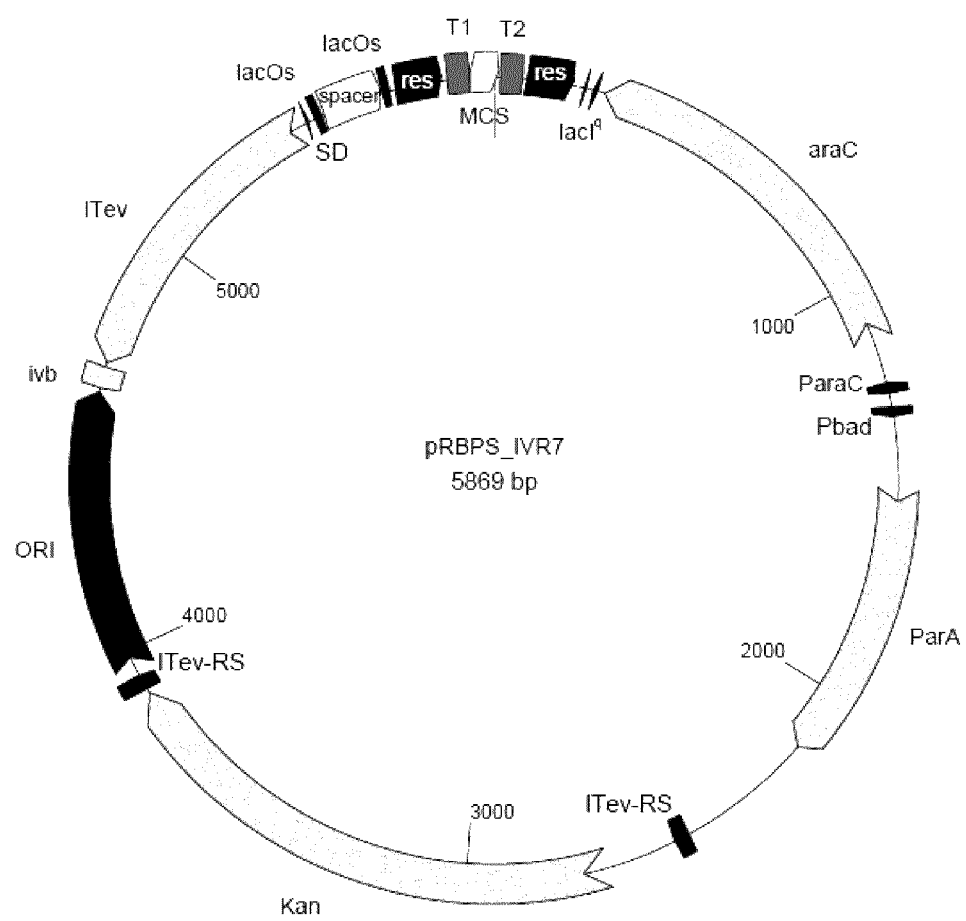
FIG. 1 is a schematic drawing of plasmid pRBPS-IVR7. T1, transcription terminator 1; MCS, multiple cloning site, T2, transcription terminator 2; res, resolution site of the ParA resolvase system; lacI$^q$, -35 and -10 region of an up-mutation of the constitutive promoter of the lacI gene of the lactose operon; araC, gene enconding the repressor of the arabinose operon; ParaC, promoter of the araC gene; Pbad, promoter of the araBAD genes of the arabinose operon; ParA, parA resolvase gene; ITev-RS, ITev restriction site; Kan, aminoglycoside 3'-phosphotransferase expression cassette conferring resistance to kanamycin; ORI, MB1 origin of replication; ivb, in vivo biotinylation sequence; ITev, intron enconded endonuclease of bacteriophage T4; SD, Shine Dalgarno sequence for ITev translation; lacOs, modified lactose operator site; spacer, spacer sequence between two direct repeats of the modified lactose operator sites lacOs.

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where the term "comprise" or "comprising" is used herein, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun e.g. "a" or "an", "the", this includes a plural form of that noun unless specifically stated. Vice versa, when the plural form of a noun is used it refers also to the singular form. For example, when endonucleases are mentioned, this is also to be understood as a single endonuclease.

Furthermore, the terms first, second, third or (a), (b), (c) and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. However, in a specific embodiment of the invention, the method steps (a), (b) and (c), optionally including any intermediate steps defined herein, are performed in chronological order.

In the context of the present invention any numerical value indicated is typically associated with an interval of accuracy that the person skilled in the art will understand to still ensure the technical effect of the feature in question. As used herein, the deviation from the indicated numerical value is in the range of ±10%, and preferably of ±5%. The aforementioned deviation from the indicated numerical interval of ±10%, and preferably of ±5% is also indicated by the terms "about" and "approximately" used herein with respect to a numerical value.

Further definitions of the terms will be given below in the context of which the terms are used.

As has been discussed above, when using an in vivo restriction system for minicircle production, an easy and efficient removal of impurities such as miniplasmids and remaining sequences of the parental plasmid is desirable. It now has been found that using the parental plasmids as well as the methods described herein, high yields of minicircles may be obtained and impurities may be removed efficiently. The in vivo restriction system described herein allows for restriction of the unwanted side-products (i.e. the miniplasmid and remaining non-recombined parental plasmid sequences) which may take place only after the production of the minicircle via recombination has been performed. Subsequently, the restricted side-products are further degraded by host exonucleases. Hence, recombination, restriction and degradation are typically performed as consecutive steps. Finally, residual miniplasmid and parental plasmid may be removed by using e.g. affinity chromatography.

This may be achieved by using a plasmid, also referred to herein as parental plasmid, comprising the following units:
  an endonuclease restriction site,
  a promoterless endonuclease expression cassette,
  a promoter,
  a sequence coding for an enzyme that catalyzes site-specific recombination,
  at least two recognition sequences for the enzyme that catalyzes site-specific recombination, and
  a sequence of interest and an element which prevents the expression of the endonuclease which are both arranged between said recognition sequences,
wherein the functional units are arranged on the plasmid such that the endonuclease expression cassette is placed under control of the promoter only after recombination at the recognition sequences for site-specific recombination.

"Parental plasmid" as used herein denotes any plasmid used for the production of minicircles. Typically, the parental plasmid has a miniplasmid region and a minicircle region.

"Miniplasmid region" as used herein denotes said portion of the plasmid described herein which will be present on the miniplasmid after site-specific recombination has occured. Within the context of the present invention, the miniplasmid region is not arranged between the sites for site-specific recombination. The miniplasmid region of the parental plasmid may carry the bacterial backbone of the plasmid, such as elements which are necessary for the stable propagation of the plasmid in the organism into which it has been transfected, elements which are necessary for removal of the miniplasmid region (e.g. miniplasmid identification sequences), marker genes, unmethylated CpG motives, cryptic expression signals, genes coding for the enzyme catalyzing the site-specific recombination and/or genes coding for the endonuclease.

In particular, the miniplasmid region of the plasmid as described herein does not comprise the sequence of interest. In one embodiment of the invention, the miniplasmid region of the plasmid described herein comprises at least one endonuclease restriction site, at least one promoterless endonuclease expression cassette, at least one promoter and/or at least one sequence coding for an enzyme catalyzing site specific recombination and/or, optionally, at least one miniplasmid identification sequence, at least one marker gene and/or at least one origin of replication and/or a gene coding for the regulator of a positively and/or negatively regulated promoter system. The miniplasmid region may furthermore comprise a Shine-Dalgarno sequence which is operably linked to the promoterless expression cassette of the endonuclease, in particular a weak Shine-Dalgarno Sequence.

"Minicircle region" as used herein, denotes the portion of the plasmid or parental plasmid described herein which will be present on the minicircle after site-specific recombination has occured. Within the context of the present invention, the minicircle region also denotes the region of the plasmid described herein which is arranged between the sites for site-specific recombination. The minicircle region of the parental plasmid comprises at least one sequence of interest (including any sequences necessary for its expression) and at least one element preventing the expression of the endonuclease. It is to be understood that the minicircle region and, thus, the resulting minicircle typically should not comprise any sequences which are considered to be unwanted for therapeutic purposes, e.g. antibiotic resistance genes, which upon administration could lead to the propagation of the antibiotic resistance in bacteria present in the human or animal to which the minicircle is adminstered.

In particular, the minicircle region does not comprise an endonuclease restriction site, a promoterless endonuclease expression cassette, a promoter not necessary for the expression of the sequence of interest, and/or a sequence coding for an enzyme that catalyzes site-specific recombination. The resulting minicircle may, however, include a sequence resulting from recombination, e.g. remainders (remaining bases) of the at least two recognition sequences for the enzyme catalyzing site-specific recombination or at least one recognition sequence for the enzyme that catalyzes site-specific recombintion (such as one res-site).

Upon expression of the enzyme that catalyzes site-specific recombination the parental plasmid is divided into a minicircle comprising the sequence of interest and the element preventing expression of the endonuclease and a miniplasmid comprising the endonuclease restriction site, the endonuclease expression cassette, the promoter and the sequence coding for a recombinase.

The term "recognition sequence for an enzyme that catalyzes site-specific recombination" relates to a sequence which is recognized by the enzyme that catalyzes site-specific recombination, in particular by a recombinase used and, correspondingly, at which recombination occurs. The fact that at least two recognition sequences for an enzyme that catalyzes site-specific recombination are present on the plasmid of the invention means, that the recognition sequences are arranged in such a way that the enzyme that catalyzes site-specific recombination catalyzes the production of a minicircle and a miniplasmid as defined above. The recognition sequences for an enzyme that catalyzes site-specific recombination will be selected in accordance with the enzyme that catalyzes site-specific recombination used. Depending on the exemplary enzymes mentioned below, the recognition sequences for the enzyme catalyzing site-specific recombination may thus be selected from the group consisting of ParA resolution sites (res-sites), attB and attP for φλ integrase or φCh31 integrase, γδ res sites, hixL, hixR, lox sites, FRT sites, Tn3 res sites, Tn21 res sites and/or cer sites. In one embodiment of the plasmid described herein, the recognition sites for the enzyme catalyzing site-specific recombination are ParA resolution sites (res-sites).

"Enzyme that catalyzes site-specific recombination" as used herein denotes any protein which allows for recombination between particular recognition sequences for said enzyme. Accordingly, a "sequence coding for an enzyme that catalyzes site-specific recombination" is a sequence coding for the respective functional enzyme that catalyzes site-specific recombination. In one embodiment of the invention, the enzyme that catalyzes site-specific recombination is a recombinase and/or an integrase. Exemplary enzymes which may be used according to the present invention are selected from the group consisting of the ParA resolvase of plasmid RK2 or RP4, φλ integrase, φCh31 integrase, γδ resolvase, Hin recombinase, φP1 Cre, yeast 2 micron Flp, Tn3 resolvase, Tn21 resolvase and XerCD. In one embodiment, the plasmid described herein comprises a sequence coding for a ParA resolvase of plasmid RK2 or RP4.

The plasmid described herein furthermore comprises a promoter. It is understood that promoter denotes any regulatory element which allows for a transcription of the sequence under control of said promoter, e.g. of the sequence which is operably linked to said promoter. The promoter used in the plasmid according to the invention can be a constitutive or a positively and/or negatively regulated promoter.

Constitutive promoters are unregulated promoters which allow for continuous transcription of the sequence which is operably linked thereto. Examples of genes expressed by constitutive promoters in *E. coli* include the genes coding for ribosomal RNAs (rrnA-H), gyrB (a subunit of the DNA gyrase), tat genes (components for tat depended protein export), the beta-lactamase gene (bla), the glyceraldehyde-3-phosphate dehydrogenase gene (gadph) or the lacI gene coding for the repressor of the lactose operon LacI. A mutation in the sequence of this latter constitutive promoter results in the lacI$^q$ promoter sequences which provides a tenfold higher protein level compared to the native lacI promotor. In one embodiment of the plasmid described herein, the promoter is lacI$^q$.

Positively regulated promoters show increased activity in the transcription of the sequence operably linked thereto, when the relevant regulator(s) is/are active. Contrary thereto, negatively regulated promoters show a decreased activity in the transcription of the sequence operably linked thereto, when the relevant regulator(s) is/are active. It is understood that promoters may also be positively and negatively regulated (i.e. multi-regulated promoters). Such positively and/or negatively regulated promoters are e.g. $P_{BAD}$, lac, trc, tac, trp, $\lambda P_L$, $\lambda P_R$, T7, tetA, phoA, cspA, rha$P_{BAD}$ and/or Pm. For instance, $P_{BAD}$ is an arabinose inducible promoter which will inhibit the transcription of the sequence operably linked thereto as long as no arabinose is present in the culture broth. Upon addition of arabinose, the sequence operably linked to the promoter will be transcribed. The ara operon is a complex (or multi) regulated operon that demonstrates both negative and positive control. The relevant regulator AraC represses transcription in the absence of arabinose and helps to activate transcription from the $P_{BAD}$ promoter in the presence of arabinose.

The plasmid described herein may comprise at least one promoter, at least two promoters, at least three promoters, at least four promoters or at least five promoters. These promoters may be independently selected from the group consisting of constitutive and positively and/or negatively regulated promoters. In particular, the promoters may be independently selected from the groups of promoters specifically mentioned herein, i.e. they may be independently selected from the group consisting of the promoter regulating the expression of the *E. coli* gene coding for ribosomal RNAs (rrnA-H), gyrB (a subunit of the DNA gyrase), tat genes (components for tat depended protein export), the beta-lactamase gene (bla), and/or the glyceraldehyde-3-phosphate dehydrogenase gene (gadph), the lacI promoter and/or the lacI$^q$ promoter and/or from the group consisting of $P_{BAD}$, lac, trc, tac, trp, $\lambda P_L$, $\lambda P_R$, T7, tetA, phoA, cspA, rhaP$_{BAD}$ and/or Pm. In one embodiment, the plasmid comprises at least two promoters independently selected from the group consisting of constitutive and positively and/or negatively regulated promoters. In one embodiment, the plasmid described herein may comprise at least one constitutive promoter independently selected from the group consisting of the promoter regulating the expression of the *E. coli* gene coding for ribosomal RNAs (rrnA-H), gyrB, tat genes, the beta-lactamase gene (bla) and/or the glyceraldehyde-3-phosphate dehydrogenase gene (gadph), the lacI promoter and/or the lacI$^q$ promoter and at least one positively and/or negatively regulated promoter selected from the group consisting of $P_{BAD}$, lac, trc, tac, trp, $\lambda P_L$, $\lambda P_R$, T7, tetA, phoA, cspA, rhaP$_{BAD}$ and/or Pm. In one of its embodiments, the plasmid described herein will thus comprise at least a lacI$^q$ promoter and a $P_{BAD}$ promoter.

The at least two promoters may be arranged on the plasmid in such a way that one promoter is operably linked to the sequence coding for the enzyme that catalyzes site-specific recombination, while the other one is arranged on the plasmid in such a way that upon recombination at the recognition sequences for the enzyme that catalyzes site-specific recombination it is operably linked to the sequence coding for the endonuclease. Hence, upon excision of the minicircle, the promoterless endonuclease expression cassette will be operably linked to said promoter. This specific arrangement of elements on the plasmid leads to an activation of the endonuclease expression cassette after the removal of the minicircle region from the parental plasmid through the recombination process. As a result of the recombination event, the promoter is operably linked with the promoterless endonuclease expression cassette, thereby allowing the expression of the enzyme. Therefore, recombination and restriction are coordinated, consecutive processes and no additional induction step is needed for the expression of the endonuclease.

In one of its embodiments, the plasmid described herein comprises a positively and/or negatively regulated promoter operably linked with the sequence coding for an enzyme that catalyzes site-specific recombination. In particular, the positively and/or negatively regulated promoter operably linked with the sequence coding for an enzyme that catalyzes site-specific recombination is selected from the group consisting of $P_{BAD}$, lac, trc, tac, trp, $\lambda P_L$, $\lambda P_R$, T7, tetA, phoA, cspA, rhaP$_{BAD}$ and/or Pm. In one of its embodiments, the plasmid described herein comprises a $P_{BAD}$ promoter operably linked with the sequence coding for an enzyme that catalyzes site-specific recombination, which is optionally a sequence coding for the ParA Resolvase.

In a further embodiment, the plasmid described herein comprises a constitutive promoter which will be operably linked to the promoterless endonuclease expression cassette after recombination has taken place. This constitutive promoter may be selected from the group consisting of the promoter regulating the expression of the *E. coli* genes coding for ribosomal RNAs (rrnA-H), gyrB, tat genes, the beta-lactamase gene (bla) and/or the glyceraldehyde-3-phosphate dehydrogenase gene (gadph), the lacI promoter and/or the lacI$^q$ promoter. For example, this constitutive promoter is the lacI$^q$ promoter.

In yet another embodiment of the plasmid described herein, the plasmid comprises a positively and/or negatively regulated promoter operably linked with the sequence coding for an enzyme for site-specific recombination and a constitutive promoter, which will be operably linked with the promoterless endonuclease expression cassette after recombination has taken place. In particular, the positively and/or negatively regulated promoter may be selected from the group consisting of $P_{BAD}$, lac, trc, tac, trp, $\lambda P_L$, $\lambda P_R$, T7, tetA, phoA, cspA, rhaP$_{BAD}$ and/or Pm and the constitutive promoter may be selected from the group consisting of the promoter regulating the expression of the *E. coli* gene coding for ribosomal RNAs (rrnA-H), gyrB, tat genes, the beta-lactamase gene (bla) and/or the glyceraldehyde-3-phosphate dehydrogenase gene (gadph), the lacI promoter and/or the lacI$^q$ promoter. In a specific embodiment, the plasmid described herein comprises a $P_{BAD}$ promoter which is operably linked with the sequence coding for an enzyme for site-specific recombination and a lacI$^q$ promoter which will be operably linked with the promoterless endonuclease expression cassette after recombination has taken place.

In an alternative embodiment of the plasmid described herein, the plasmid comprises a positively and/or negatively regulated promoter operably linked with the sequence coding for an enzyme for site-specific recombination and a positively and/or negatively regulated promoter which will be operably linked with the promoterless endonuclease expression cassette after recombination has taken place. In a specific embodiment, the promoter operably linked with the promoterless endonuclease expression cassette after recombination has taken place is a positively regulated promoter. In a further specific embodiment, the promoter operably linked with the promoterless endonuclease expression cassette after recombination has taken place is a negatively regulated promoter. In yet a further specific embodiment, the promoter operably linked with the promoterless endonuclease expression cassette after recombination has taken place is a positively and negatively regulated promoter. The positively and/or negatively regulated promoters may be selected from any of the promoters mentioned herein.

In yet a further embodiment of the plasmid described herein, the plasmid comprises a positively and/or negatively regulated promoter operably linked with the sequence coding for an enzyme for site-specific recombination, whereby said promoter is also operably linked with the promoterless endonuclease expression cassette after recombination has taken place. In a specific embodiment of the plasmid described herein, the plasmid comprises a positively regulated promoter operably linked with the sequence coding for an enzyme for site-specific recombination, which is also operably linked with the promoterless endonuclease expression cassette after recombination has taken place. In another specific embodiment of the plasmid described herein, the plasmid comprises a negatively regulated promoter operably linked with the sequence coding for an enzyme for site-specific recombination, which is also operably linked with the promoterless endonuclease expression cassette after recombination has taken place. In yet a further specific embodiment of the plasmid described herein, the plasmid comprises a positively and negatively regulated promoter operably linked with the sequence coding for an enzyme for site-specific recombination, which is also operably linked with the promoterless endonuclease expression cassette after recombination has taken place. The positively and/or negatively regulated promoters may be selected from any of the promoters mentioned herein.

It is however understood, that the plasmid described herein may, in addition to the two promoters mentioned above which allow for a regulation or coordination of recombination and restriction, comprises further promoters, e.g. promoters suitable for regulating the transcription of the sequence(s) of interest, for regulating the transcription of marker genes which are optionally present on the plasmid and/or for regulating the transcription of further sequences which are optionally present on the plasmid.

As has been described above, the plasmid described herein comprises a promoterless endonuclease expression cassette. The "promoterless endonuclease expression cassette" of the plasmid of the present invention thus relates to an expression cassette comprising a sequence coding for an endonuclease as described herein and optionally a terminator, ribosome binding sites and/or other elements necessary for its expression as a functional enzyme. Such other elements necessary for the expression of a functional enzyme may include a Shine-Dalgarno sequence, e.g. a weak Shine-Dalgarno sequence. In prokaryotes, Shine-Dalgarno (SD) sequences, nucleotides upstream from start codons on messenger RNAs (mRNAs) that are complementary to ribosomal RNA (rRNA), facilitate the initiation of protein synthesis. The location of SD sequences relative to start codons and the stability of the hybridization between the mRNA and the rRNA correlate with the rate of synthesis. The effectiveness of an SD sequence is determined by both its base-pairing potential with the anti-SD sequence and its spacing from the start codon. The aligned spacing of the SD sequences generally varies from 5 to 13 bases, with optimal spacings of about 8 to 10 bases for E. coli genes [9, 10]. The SD sequences could be different subsequences of the complementary sequence of the anti-SD sequence however, most SD sequences are slight variations of the GGAGG core [11]. A weak SD sequence demonstrates for example variations in terms of optimal spacing and/or in terms of complementarity to the anti-SD sequence. The promoterless endonuclease expression cassette does not comprise and/or is not operably linked to a promoter allowing for its expression before site-specific recombination has occured. After site-specific recombination has occurred, the expression cassette may be operably linked to a promoter.

The sequence coding for an endonuclease denotes any sequence coding for the respective functional endonuclease, i.e. for an enzyme that cleaves the phosphodiester bonds within a polynucleotide chain, whereby cleavage occurs at specific sequences within the polynucleotide chain. Such specific sequences recognized by the endonuclease are also called restriction sites or endonuclease restriction sites. Different types, i.e. type I, type II, type III or homing endonucleases of restriction endonucleases are known in the art. As used herein, any endonuclease known in the art may be used for the purpose of the present invention. Examples of endonucleases useful in the present invention include the endonucleases selected from the group of homing endonucleases consisting of I-TevI, I-CreI, I-DmoI, I-PpoI, I-SceI and/or I-SceII. In one embodiment of the invention, the sequence coding for an endonuclease comprised on the plasmid described herein is a sequence coding for I-TevI.

Accordingly, the plasmid described herein may comprise at least one, at least two, at least three or at least four endonuclease restriction site(s). The plasmid described herein may comprise one, two, three, four, five or six endonuclease restriction site(s). In particular, it comprises two endonuclease restriction sites. The endonuclease restriction sites are arranged on the miniplasmid region of the parental plasmid or plasmid as described herein. Hence, the endonuclease restriction sites are not arranged between the recognition sequences for the enzyme catalyzing site-specific recombination, i.e. they are not arranged on the minicircle region of the parental plasmid. This arrangement allows for restriction of impurities remaining after the site-specific recombination has been performed, i.e. restriction of the miniplasmid and/or any non-recombinated parental plasmid remaining in the culture broth.

The plasmid described herein may further comprise one or more sequence(s) of interest. In one embodiment, the plasmid described herein comprises at least one, at least two, at least three or at least four sequences(s) of interest. Optionally, the plasmid described herein comprises one, two, three, four, five or six sequences(s) of interest, in particular one sequence of interest. The sequences(s) of interest will be present on the minicircle after recombination has occurred. Hence, it/they is/are arranged in the minicircle region of the plasmid described herein, i.e. it/they is/are arranged between the sequences for the enzyme catalyzing site-specific recombination.

"Sequence of interest" as used herein denotes any nucleic acid whose transcription and, optionally translation, will produce a gene product of interest, in particular a product (e.g. a protein) having a therapeutic value or therapeutic efficacy. Thus, sequence of interest also includes an expression cassette for the sequence of interest. Products of therapeutic value include products which have a therapeutic efficacy in the treatment of humans and/or animals, e.g. which may be used as vaccines for humans and/or animals. Products of therapeutic value, however, also includes products which can be detected in the human and/or animal after the minicircle has been administered, thus allowing to determine e.g. the level of a specific protein in said human and/or animal.

It is to be understood, that "therapeutic value" or "therapeutic efficacy" when used in the context of the present invention denotes that the product may be useful in the treatment, prevention and/or diagnosis of a disease to be treated. Thus, the product of therapeutic value may lead to full or partial remission of the symptoms of the disease to be treated, it may prevent the outbreak of a disease to be treated, may prevent the occurrence of some symptoms of the disease to be treated, may reduce the severity of the disease to be treated, change the course of disease to be treated and/or may be useful in diagnosis of the disease to be treated.

Sequences of interest which may be present on the plasmid described herein include sequences coding for proteins, enzymes, hormones, lymphokines, antigens, reporter genes, growth factors, fragments of proteins such as epitopes, sequences for RNA interference and/or antisense sequences (e.g. antisense RNA sequences). It is understood, that the sequences(s) of interest may include any sequence which codes for a product which is therapeutically useful itself, such as a hormone which has to be substituted in a human and/or animal. However, sequences(s) of interest may also exert their effect on the protein or RNA level of the human and/or animal to be treated. E.g., the sequences(s) of interest may code for antisense RNA or ribozymes or encode a protein which affects the level of another protein within the cell treated. Sequences(s) of interest may also include any sequence which mediates killing of the cells, e.g. by selectively rendering the cells sensitive to certain drugs. Of course, sequences(s) of interest present on the plasmid described herein may also be (a) sequence(s) which may be used for vaccinating the human and/or animal to which it is administered, e.g. sequence(s) coding for an antigen which is capable of generating an immune response in the human and/or animal treated. This includes antigens generating immune responses against viruses (e.g. Eppstein-Barr, HIV, Hepatitis), against bacteria and/or against tumors.

The plasmid described herein further comprises an element preventing the expression of the endonuclease, e.g. a terminator or an operator. In particular, the plasmid described herein comprises at least one, at least two, at least three, at least four or at least five element(s) preventing the expression of the endonuclease. In one embodiment, the plasmid described herein comprises one, two, three, four, five, six, seven, eight, nine or ten element(s) preventing the expression of the endonuclease. In one embodiment of the plasmid described herein, at least one, at least two, at least three or at least four element(s) preventing the expression of the endonuclease present on the plasmid described herein are arranged between the recognition sequences for the enzyme catalyzing site-specific recombination. Optionally, one, two, three or four element(s) preventing the expression of the endonuclease is/are arranged between the recognition sequences for the enzyme that catalyzes site-specific recombination of the plasmid described herein, i.e. the element(s) preventing the expression of the endonuclease is/are arranged in the minicircle region of the plasmid. In one embodiment, the element(s) preventing the expression of the endonuclease is/are (a) terminator(s). In another embodiment, the element(s) preventing the expression of the endonuclease is/are (a) operators(s). It is, however, to be understood that in this embodiment the plasmid may comprise further terminators and/or operators considered necessary by the person skilled in the art, which are not arranged between the recognition sequences for the enzyme catalyzing site-specific recombination. Accordingly, this/these further terminator(s) and/or operator(s), if present, will be arranged in the miniplasmid region of the plasmid described herein.

As already discussed above, this arrangement of the element(s) preventing the expression of the endonuclease between the recognition sequences for the enzyme for site-specific recombination permits recombination and restriction to take place sequentially. This is due to the fact that only after the recombination event removing the minicircle region from the parental plasmid, a promoter will be operably linked to the promoterless endonuclease expression cassette, while prior to the recombination event the transcription from the promoter, which will be later on operably linked to the promoterless endonuclease expression cassette, will be terminated at the element(s) preventing the expression of the endonuclease present between the recognition sequences for the enzyme for site-specific recombination.

Furthermore, no additional induction step is necessary for restriction as the promoter that is operably linked to the endonuclease expression cassette by the recombination process is a constitutive promoter or an activated negatively and/or positively regulated promoter.

Bacteria and their phages use two main modes of terminating transcription: Rho-independent or 'intrinsic' termination, mainly requiring elements located on the mRNA, and Rho-dependent termination, relying on both mRNA elements and trans-acting factors. Examples for Rho-dependent termination include the trp operon in *E. coli, E. coli* colE1 gene or the cro gene of phage lambda. Examples for Rho-independent transcription terminators in *E. coli* are rrnBT1 (terminators of rRNA operons), the terminator of the lpp gene (outer membrane lipoprotein), the terminators of rpoC (the gene that codes for the beta' subunit of RNA polymerase) or rpoD (the gene which codes for the sigma subunit of RNA polymerase). In one embodiment, the terminator(s) used in the plasmid described herein is/are selected from the group of Rho-independent transcription terminators consisting of rrnBT1, the terminator of the lpp gene, the terminators of rpoC and/or rpoD. In one embodiment, the transcription terminators present on the plasmid described herein are rrnBT1 and/or rpoC.

Suitable operator sites used in the plasmid described herein are derived from negatively controlled inducible (lactose, tetracycline) or repressible operons (tryptophan) or operons that are using both positive and negative control e.g. arabinose where AraC acts as well as a positive and a negative regulator.

The plasmid according to the present invention may furthermore comprise an origin of replication (ORI). As used herein, ORI denotes any sequence at which replication can be initiated. In particular, ORI refers to a sequence on the plasmid allowing the plasmid to replicate independently of the genome of the organism in which it has been transfected. The ORI present in the plasmid of the invention may be a prokaryotic ORI. Various prokaryotic ORIs are known to the person skilled in the art, who will be able to select a suitable ORI according to the bacteria culture, the culture conditions and the type of plasmid used a suitable ORI. Exemplary prokaryotic ORIs which may be used according to the present invention include ColE1, p15A, pSC101 and/or pMB1. In one embodiment, the prokaryotic ORI present on the plasmid described herein is pMB1 of plasmid pUC19.

The plasmid as described herein may further comprise at least one, at least two, at least three, at least four or at least five identification sequence(s). As used herein "identification sequence" denotes any sequence which is suitable to identify and/or isolate the miniplasmid and/or the minicircle resulting from site-specific recombination and/or the non-recombined parental plasmid. In one specific embodiment, the identification sequence is a miniplasmid identification sequence. In another specific embodiment, the identification sequence is a minicircle identification sequence. In another embodiment of the plasmid described herein, the plasmid comprises a miniplasmid identification sequence and a minicircle identification sequence. It is to be understood that, when a minicircle identification sequence and a miniplasmid identification sequence are present on the plasmid described herein, they may be different sequences in order to allow for identification and thus a specific isolation of the miniplasmid and the minicircle. Accordingly, if one identification sequence is present on the miniplasmid, it is not present on the minicircle and vice versa.

The identification sequence may be a sequence present on the plasmid capable to bind to a specific ligand. The ligand can be any ligand considered suitable by the person skilled in the art for identification and/or isolation of the miniplasmid, the minicircle and/or the non-recombined parental plasmid. Exemplary ligands to which the isolation sequence specifically binds include proteins, chemical ligands and nucleic acid ligands. "Specifically binding" as used herein, denotes any type of sequence-ligand interaction, which is not random and sufficiently stable in order to allow for a reliable identification and/or isolation of the minicircle, miniplasmid and/or non-recombined parental plasmid.

In one of its embodiments, the identification sequence present on the plasmid described herein is a sequence capable to specifically bind to a protein. Thus, the identification sequence capable of specifically binding to a specific protein forms a stable DNA-protein complex with its ligand. Specifically, the identification sequence which the plasmid described herein comprises may be a lac operator site. This lac operator site binds specifically to a LacI repressor protein, thus allowing for identification and/or isolation of the minicircle and the non-recombined parental plasmid or the miniplasmid and the non-recombined parental plasmid.

It is understood that the identification sequence may also comprise at least one, at least two, at least three, at least four or at least five repeats of the lac operator site, optionally including a spacer between the repeats of the operator sites.

In one embodiment, the identification sequence may be a modified lac operator site, in particular at least two, at least three, at least four or at least five repeats of the modified lac operator sites, optionally including a spacer between the repeats of the lac operator sites. In a specific embodiment, the identification sequence consists of two repeats of the modified lac operator sites which are linked by a spacer (lacOs). A lacOs site is a symmetric version of the lacO sequence that binds the lactose repressor of Escherichia coli 10-fold more tightly than does the natural lactose operator sequence. This tight-binding operator is an inverted repeat of a 15-base-pair segment from the left half of the natural operator sequence [12]. The native lactose repressor is known to acts as a tetramer of identical subunits whereas two subunits interact with a single lactose operator site. Therefore, a complex consisting of two lactose operator sites and four lactose repressor proteins can be established. If two lactose operator sites are involved, they are separated by a spacer sequence allowing loop formation in order to enable the proper interaction of these two lactose operator sites with the subunits of the tetrameric lactose repressor. This spacer sequence may be any unrelated or a related sequence (e.g. the lactose operator site itself or multiple copies thereof, respectively).

It is understood, that the plasmid as described herein may include one, two, three, four or five separate identification sequence(s). In one embodiment, the plasmid as described herein comprises at least two miniplasmid identification sequences, optionally at least two lac operator sites as described herein or modified lac operator sites as described herein specifically binding to a LacI repressor protein.

The plasmid as described herein may further comprise at least one marker sequence. In one embodiment of the plasmid described herein, it comprises one, two, three, four of five marker sequence(s). In particular, the plasmid described herein comprises one marker sequence. The marker sequence may be any of the well-known sequences which are used for being able to detect bacteria comprising the plasmid described herein or to control the growth of bacteria comprising the plasmid described herein compared to bacteria which have not been transfected with the plasmid described herein. For example, antibiotic resistance genes, heavy metal resistances, auxotrophic selection markers, genes which produce a substance necessary for bacterial growth, etc. may be used according to the present invention. In one of its embodiments, the plasmid described herein comprises a marker sequence coding for an antibiotic resistance. Sequences coding for antibiotic resistance include e.g. sequences coding for ampicillin, tetracycline, chloramphenicol resistance and/or kanamycin resistance. In one embodiment of the plasmid described herein, the marker sequence is a sequence coding for kanamycin resistance.

It is understood by the person skilled in the art, that alternatively to marker sequences, the plasmid described herein may also comprise features allowing to select bacteria comprising the plasmid described herein. Such features may comprise selection systems which are not based on resistance or complementation but rather on the suppression of a kill mechanism. Cranenburgh et at for example developed a host/vector system where the endogenous dapD locus (essential for diaminopimelate synthesis and therefore for cell wall synthesis) was replaced by dapD under the control of lactose promoter/operator system [13]. Transformation of this host strain with the corresponding plasmid carrying lactose operator sites results in binding of the cellular lactose repressors (lacI) to the plasmid DNA. This competitive titration of the lacI protein allows the expression of the dapD gene from the lac promoter and thereby synthesis of a functional cell wall. This system ensures killing of plasmid-free cells except the culture medium is supplemented with IPTG. More recently Mairhofer et at described a system which uses the RNA I of the ColE1 origin of replication to suppress the translation of the repressor of the tetracycline promoter/operator system which in turn suppresses the expression of the murA gene which is essential for cell wall synthesis [14]. The system is based on an E. coli strain carrying the murA gene (UDP-N-acetylglucosaminidase enolpyruyl transferase) under the control of the tetracycline promoter/operator system. The gene encoding the tetracycline repressor was modified in a way that the 5' untranslated region of the repressor mRNA is partially complementary to the RNA I of the ColE1 origin. Binding of RNA I to the mRNA inhibits the translation into the repressor protein thereby allowing expression of the murA gene. Therefore, in this case only cells bearing plasmids with the ColE1 origin of replication are able to survive.

Further sequences considered suitable by the person skilled in the art may be present in the plasmid described herein, in particular in the miniplasmid region of the parental plasmid. Such sequences include e.g. sequences coding for the regulators of positively and/or negatively regulated promoters such the AraC, LacI, TrpR, $\lambda cI_{857}$, PhoB, PhoR, RhaR, RhaS, TetR or the XylS protein.

As has been described above, the parental plasmid described herein may be used for the production of minicircles comprising one or more sequence(s) of interest.

Another aspect of the present invention thus relates to a method for providing a minicircle, comprising the following steps:
a) transfecting a plasmid as described herein in an organism capable to replicate said plasmid,
b) recombinating at the recognition sequences for the enzyme catalyzing site-specific recombination, in order to obtain a minicircle comprising the sequence of interest and the element that prevents the expression of the recombinase and a miniplasmid comprising the endonuclease restriction site, the endonuclease expression cassette, the promoter and the sequence coding for an enzyme catalyzing site-specific recombination,
c) purifying the minicircle.

Transfection of the plasmid in an organism capable to replicate said plasmid may be performed by any method known in the art, e.g. transformation, electroporation, conjugation and/or protoplast transformation.

The organism capable of replicating the plasmid described herein may be any organism considered suitable by the person skilled in the art. Organism capable of replicating the plasmid as used herein also includes the organism itself (i.e. the host) as well cells derived therefrom (i.e. host cells). It is thus understood by the person skilled in the art, that the method described herein may be carried out in vivo or in vitro.

The method described herein may be carried out in any host and/or host cell considered suitable by the person skilled in the art. For simplicity, any reference to a host cell is also to be understood to also denote a reference to the respective host from which cells may be derived. Host cells include bacterial and eukaryotic cells (such as yeast cells, human cells, animal cells and/or plant cells). Exemplary bacterial cells include Escherichia coli, Bacillus subtilis, Agrobacterium tumefaciens, Pseudomonas sp. and/or Clostridium sp. cells. In one embodiment of the method described herein, the host cell is derived from E. coli. Examples of yeast cells which may be used in the method of the present invention include Saccharomyces sp. and/or Kluyveromyces sp. cells. Examples of eukaryotic cells which may be used in the method of the present invention include CHO and COS cells.

After transfection of the plasmid as described herein into an organism capable to replicate said plasmid, replication of the plasmid up to the desired level will be performed. Such a desired level of plasmid in the cell may be the level at which the replication of the plasmid in the cell reaches a plateau. This level may vary with the origin of replication used. In the case of the pMB1 orgin of replication derived from plasmid pUC19, exemplary levels of plasmid per cell are about 500-700 copies per cell, in particular about 500, 600 or 700 copies per cell.

In step b) of the method described herein, recombination at the recognition sequences for site-specific recombination takes place. By recombinating at said sequences, a minicircle comprising the sequence of interest and the element preventing the expression of the endonuclease and a miniplasmid comprising the endonuclease restriction sites, the endonuclease expression cassette, the promoter and the sequence coding for an enzyme that catalyzes site-specific recombination are produced.

In one embodiment, step b) of the method described herein comprises an induction of the expression of the sequence coding for the enzyme that catalyzes the site-specific recombination. The induction in step b) may also include the removal of any factors repressing the expression of the sequence coding for the enzyme that catalyzes site-specific recombination. Thus, if step b) of the method described herein comprises an induction of the expression of the sequence coding for the enzyme catalyzing site-specific recombination, the plasmid may comprise a positively and/or negatively regulated promoter as described herein operably linked with the sequence coding for the enzyme catalyzing the site-specific recombination. It is understood by the person skilled in the art, that depending on the type of positively and/or negatively regulated promoter used, induction may take place e.g. via adding a certain compound to the culture broth, limiting the availability of a certain compound in the culture broth, changing the temperature and/or changing the pH-value in the culture broth and/or inducing the expression of a protein necessary for the transcription of the desired sequence or the uptake of a certain compound present in the culture broth. In one embodiment of the method described herein, induction is achieved by adding arabinose, IPTG, lactose, tryptophan, T7 polymerase, tetracycline, m-toluic acid and/or rhamnose to the culture broth, by changing the temperature of the culture broth and/or by limiting the phosphate availability in the culture broth. This ways of inducing the expression of the sequence coding for the enzyme catalyzing the site-specific recombination may be in particular suitable if the positively and/or regulated negatively promoter is selected from the group consisting of $P_{BAD}$, lac, trc, tac, trp, $\lambda P_L$, $\lambda P_R$, T7, tetA, phoA, cspA, rhaP$_{BAD}$ and/or Pm. In one embodiment of the method described herein, step b) comprises adding arabinose to the culture broth, thus inducing expression of the sequence coding for the enzyme that catalyzes the site-specific recombination. Induction of the expression of the sequence coding for an enzyme catalyzing site-specific recombination via arabinose is in particular suitable, if the plasmid comprises an arabinose inducible promoter such as $P_{BAD}$.

In one embodiment of the method described herein, between step b) and c) restricting the miniplasmid by means of the endonuclease is performed.

As has already been described above, after recombination at the at least two recognition sequences for the enzyme catalyzing site-specific recombination, the promoterless endonuclease expression cassette is operably linked to a promoter, thus allowing expression of the endonuclease. Hence, after site-specific recombination, restriction of the miniplasmid at the endonuclease restriction sites is performed by means of the endonuclease. It is to be understood that also remaining non-recombined parental plasmids will be restricted by the endonuclease, since the parental plasmids also comprise an endonuclease restriction site, while the minicircles obtained will not be restricted. Hence, in one embodiment of the method described herein, between step b) and c) restricting the miniplasmid and/or the non-recombined parental plasmid by means of the endonuclease is performed. The method disclosed herein therefore allows for the restriction of impurities without affecting the minicircles produced.

As can be derived from the above, the method described herein comprises a successive recombination and restriction without the need of performing any additional induction steps in order to allow for restriction.

The method described herein further comprises step c) of purifying the minicircle.

Purification of the minicircle may be performed by using standard techniques for plasmid DNA purification. Such purification methods include purification on a cesium chloride density gradient in the presence of ethidium bromide, use of anion exchange columns and/or the use affinity chromatography.

Standard techniques for plasmid DNA purification may include the following process steps: 1) Cell lysis (mechanical, enzymatic, chemical or heat lysis), 2) removal of cell debris by centrifugation, filtration or expanded bed chromatography, 3) removal of host contaminations (i.e. proteins, RNA, chromosomal DNA, endotoxins) by e.g. RNase and/or proteinase K treatment, organic solvents like phenol and chloroform, salting out or PEG precipitation, 4) plasmid enrichment by alcohol or PEG precipitation and 5) finally plasmid purification by ultracentrifugation (e.g. cesium chloride density gradient centrifugation) or chromatographic techniques including ion exchange, size exclusion, hydrophobic interaction chromatography, reversed-phase chromatography or any kind of affinity chromatography suitable for purifying plasmid DNA.

It is understood that purification of the minicircle in step c) of the method described herein may also include purifying plasmid DNA from the culture broth.

In one of its embodiments step c) of the method described herein involves purification of the minicircle by removing the miniplasmid(s) and/or the non-recombined parental plasmid(s).

Thus, step c) also comprises the removal of the miniplasmid(s) and/or the non-recombined parental plasmid(s) by affinity chromatography. Hence, the identification sequences present on the miniplasmid(s) and/or the non-recombined parental plasmid will be used for purification in step c) of the method described herein. It is understood, that in this embodiment, the miniplasmid(s) and/or the non-recombined parental plasmid(s) will comprise identification sequences not present in the minicircle(s), i.e. the minicircle(s) will comprise either no or a different identification sequence than the miniplasmid(s) and/or non-recombined parental plasmid(s).

The identification sequence present on the miniplasmid(s) and/or the non-recombined parental plasmid may be a sequence capable to bind to a specific ligand. The ligand can be any ligand considered suitable by the person skilled in the art for identification and/or isolation of the miniplasmid(s) and/or the non-recombined parental plasmid(s). Exemplary ligands to which the isolation sequence specifically binds include proteins, chemical ligands and nucleic acid ligands. In one of the embodiments of the method described herein, the identification sequence present on the miniplasmid(s) and/or the non-recombined parental plasmid is a sequence capable to specifically bind to a protein. Thus, the identification sequence capable of specifically binding to a specific protein forms a stable DNA-protein complex with its ligand. It is understood that any identification sequence described herein may be used. Specifically, the identification sequence which the miniplasmid(s) and/or the non-recombined parental plasmid(s) comprise(s) may be a lac operator site, optionally a modified lac operator site (lacOs) as described herein. This lac operator site binds specifically to a LacI repressor protein, thus allowing for identification and/or isolation of miniplasmid and/or the parental plasmid and therefore for the purification of the minicircle.

In one embodiment, the miniplasmid(s) and/or the non-recombined parental plasmid(s) comprise(s) at least two miniplasmid isolation sequences, optionally at least two lac operator sites or modified lac operator sites (lacOs) specifically binding to a LacI repressor protein.

Accordingly, when performing affinity chromatography, the minicircle(s) will be present in the flow through of the affinity chromatography, while the miniplasmid(s) and/or the non-recombined parental plasmid(s) will be bound to the matrix of the column used.

The column may for instance be a column with an ion exchange matrix or a matrix for hydrophobic interaction chromatography, or for size exclusion chromatography, respectively, etc. In principle, any chromatography process may be employed, which is suitable for isolating DNA molecules. If, for instance, (a) lac operator site(s) is/are used for as isolation sequences, the matrix will comprise a LacI repressor protein to which those sequences specifically bind.

Subsequently, the miniplasmid(s) and/or the non-recombined parental plasmid(s) may be eluted from the column. Elution from the column may for instance be performed by adding IPTG. Thus, the column is regenerated and may again be used for purification.

It is to be understood that in one embodiment of the method described herein, the above described purification step by means of using a miniplasmid identification sequence present on the miniplasmid and/or the non-recombined parental plasmid, also includes removing the non-recombined parental plasmid(s) and/or the miniplasmid by using the miniplasmid identification sequence(s) as described above. Furthermore it may also include digestion of the non-recombined parental plasmid and/or miniplasmid which has/have been restricted by the endonuclease. Digestion of the cut parental plasmid and/or miniplasmid may be performed by enzymes such as exonucleases present in the host cell.

The use of one of the above described purification steps further improves the minicircle yield achieved by the method described herein.

A further aspect of the invention relates to a minicircle produced according to the method described herein.

Depending on the sequence(s) of interest used, the minicircles derived from the plasmid described herein and/or by the method described herein may be used in the treatment and/or prevention of different diseases in an animal and/or human.

As used herein "treatment" includes any treatment of an animal and/or human which leads to a full or partial remission and/or alleviation of the symptoms or the disease to be treated. "Prevention" includes any treatment of an animal and/or human which fully or partially prevents the outbreak of a disease which should be prevented and/or any symptoms thereof.

A further aspect of the invention therefore relates to a pharmaceutical composition comprising the minicircle produced according to the method described herein and/or derived from the plasmid described herein and at least one pharmaceutically acceptable excipient.

In the context of the present invention "pharmaceutically acceptable" relates to any compound which may be used in a pharmaceutical composition without causing any undesired effects (such as negative side effects) in a patient to which the composition is administered.

Pharmaceutically acceptable excipients which may be present in the pharmaceutical composition as described herein include fillers, binders, lubricants, glidants, surfactants, pore formers, release-rate modifiers, anti-tacking agents, diluents and any further excipient considered suitable by the person skilled in the art.

The pharmaceutical composition described herein may be in the form of a solid dosage form or in the form of a fluid dosage form. Accordingly, it may be administered by any administration route considered suitable by the person skilled in the art, such as oral, e.g. as solid or fluid oral dosage form, or parenteral, e.g. via injection or infusion.

The amount of minicircles present in the pharmaceutical composition described herein will depend on the sequence(s) of interest present on the minicircle(s), the disease to be treated and/or prevented and the mode of administration.

The invention is further described in the following examples which are solely for the purpose of illustrating specific embodiments of the invention, and are also not to be construed as limiting the scope of the invention in any way.

EXAMPLES

Example 1

Material and Methods

Construction of Plasmid pRBPS-IVR7_GFPCMV

The plasmid pCMV-GFP carries the GFP gene under the control of the CMV immediate early promoter and the SV40 polyadenylation sequence [6]. Plasmid pCMV-GFP was digested with NsiI, DraI and SphI resulting in a 1833 bp fragment carrying the GFP sequence including the CMV promoter and the polyadenylation sequence, a 1070 bp and a 584 bp fragment. The 1833 bp fragment resulting from the NsiI/DraI digestion was purified after agarose gel electrophoresis. The extracted fragment was inserted in plasmid pRBPS-IVR7 digested with PstI and PmlI. The restriction enzyme PstI was chosen as NsiI and PstI produce compatible ends and DraI and PmlI produce blunt ends. The resulting plasmid pRBPS-IVR7_GFPCMV carries the GFP gene under the control of the CMV immediate early promoter and the SV40 polyadenylation between the resolution sites for ParA resolvase driven recombination (cf. FIG. 2).

Minicircle DNA Production

Figure 2:
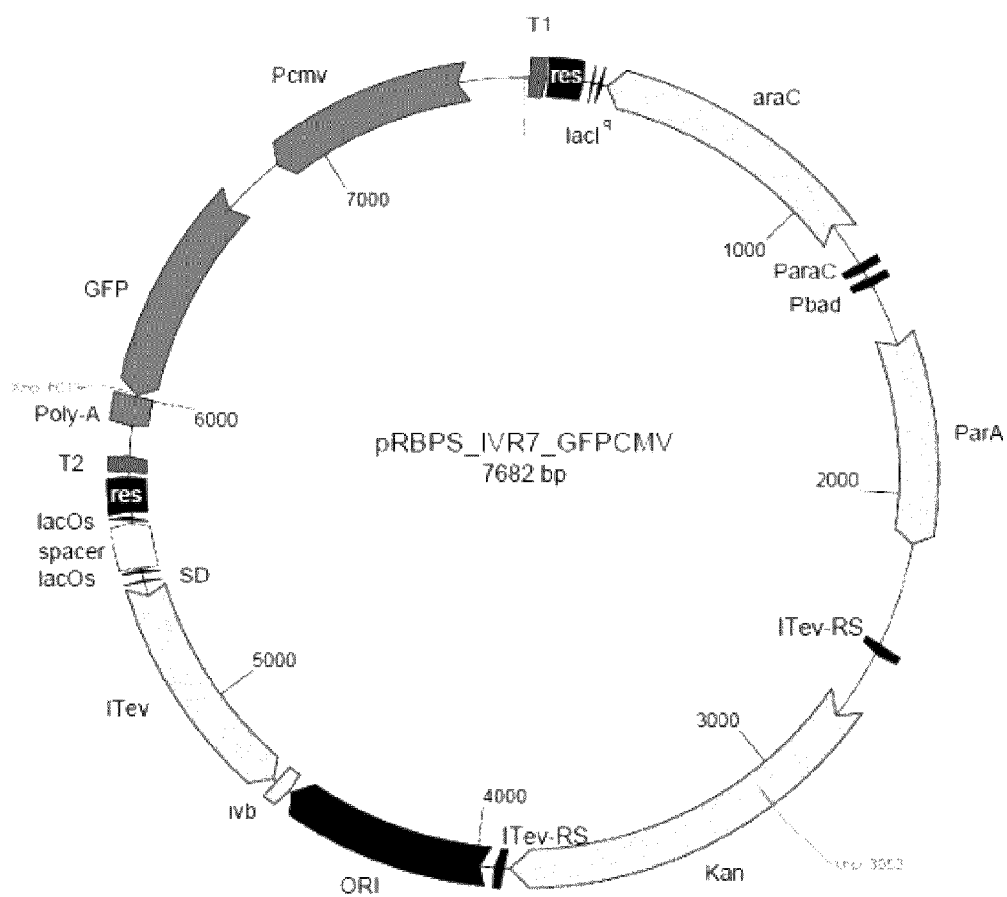
FIG. 2 is a schematic drawing of plasmid pRBPS_IVR7_GFP. T1, transcription terminator 1; res, resolution site of the ParA resolvase system; lacI$^q$, -35 and -10 region of an up-mutation of the constitutive promoter of the lacI gene of the lactose operon; araC, gene enconding the repressor of the arabinose operon; ParaC, promoter of the araC gene; Pbad, promoter of the araBAD genes of the arabinose operon; ParA, parA resolvase gene; ITev-RS, ITev restriction site; Kan, aminoglycoside 3'-phosphotransferase expression cassette conferring resistance to kanamycin; ORI, MB1 origin of replication; ivb, in vivo biotinylation sequence; ITev, intron encoded endonuclease of bacteriophage T4; SD, Shine Dalgarno sequence for ITev translation; lacOs, modified lactose operator site; spacer, spacer sequence between two direct repeats of the modified lactose operator sites lacOs; T2, transcription terminator 2; Poly-A, polyadenylation signal; GFP; green fluorescent protein; Pcmv; cytomegalovirus immediate early enhancer/promoter.

For small scale production 100 ml LB-medium supplemented with kanamycin were inoculated with 1 ml of an overnight culture of an *E. coli* strain transformed with plasmid pRBPS-IVR7_GFPCMV grown at 28° C. in LB-medium supplemented with kanamycin and 1% glucose. For large scale production 1000 ml LB-medium supplemented with kanamycin were inoculated with 10 ml of an overnight culture as described for small scale production. The parental plasmid pRBPS-IVR7_GFPCM carrying the GFP expression cassette under the control of the CMV immediate early promoter is shown in FIG. 2. The culture was cultivated at 37° C. and the expression of the ParA resolvase was induced with 0.5% L-arabinose. For optimal results in shaking flask cultures induction was accomplished in an OD600 range of 1.5 to 2. Samples were taken immediately prior to induction (t0), one hour (t1) and two hours (t2) after induction.

DNA Preparation and Analysis:

Small scale DNA preparations were performed using the peqGOLD Plasmid Miniprep Kit I from Peqlab (Erlangen, Germany). Large scale DNA preparations was performed using the NucleoBond PC 10000 Kit from Macherey & Nagel (Düren, Germany). Restriction analysis was performed with XhoI obtained from New England Biolabs (Beverly, Mass., USA) resulting in the following DNA fragments: Parental plasmid: 4722 bp and 2960 bp; miniplasmid: 5567 bp; minicircle: 2115 bp (the XhoI sites are indicated in FIG. 2). For restriction analysis after RBPS-chromatography, samples were desalted by isopropanol precipitation.

RBPS-Chromatography:

The RBPS affinity chromatography matrix was produced as described by Mayrhofer et al [6]. Affinity chromatographic purification was carried out as using an ÄKTAexplorer 100 chromatography system (GE Healthcare Bio-Sciences, Piscataway, N.J., USA) with 2 ml RBPS-Chromatography matrix in a Tricorn 10/20 column. The column was equilibrated with 5 CV 50 mM Tris pH 8, 500 mM NaCl. Prepurified minicircle-DNA (1 mg/ml in 50 mM Tris pH 8, 500 mM NaCl) was applied at a flow rate of 0.5 ml/min. After sample application the column was washed with 50 mM Tris pH 8, 500 mM NaCl at a flow rate of 1 ml/min until the UV absorbance at 260 nm decreased to a stable baseline value. Stable baseline was defined as a fluctuation of the UV260 nm signal less than 0.5 mAU over a time-frame of 5 min. The total flow-through containing the minicircle-DNA was collected and subsequently precipitated with isopropanol. The column was regenerated with 50 mM Tris pH8, 500 mM NaCl, 5 mM IPTG and washed with 5 CV 50 mM Tris pH 8, 1 M NaCl and 5 CV 50 mM Tris pH 8 before equilibrating for the next run.

Example 2

Minicircle Production

Figure 3:
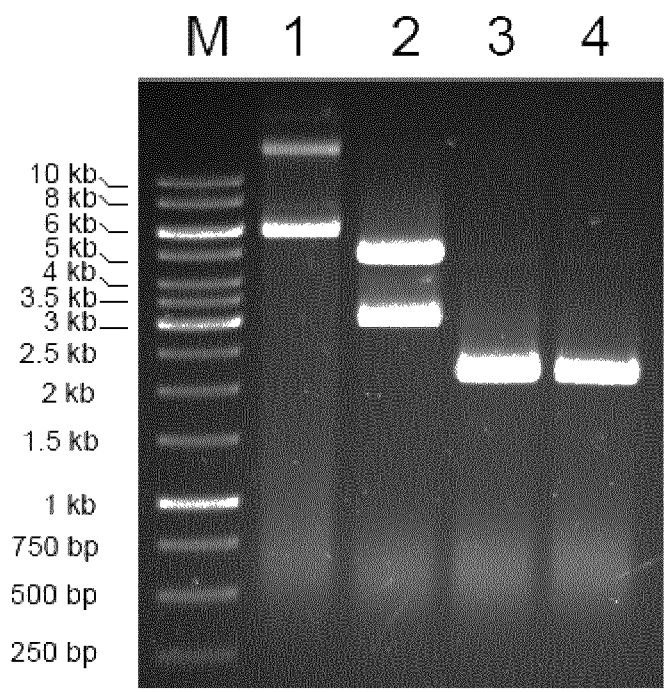
FIG. 3: Restriction analysis of GFPCMV-minicircles derived from parental plasmid pRBPS7_IVR7_GFPCMV. Digestion with XhoI resulted in a 4722 bp and a 2960 bp fragment in case of the parental plasmid and in the linearization of the miniplasmid (5567 bp) and the minicircle-DNA (2115 bp). Lane M, 1 kb DNA-ladder (GeneRuler, Fermentas); lane 1, parental plasmid pRBPS7_IVR7_GFPCMV undigested; lane 2, XhoI digested plasmid-DNA (1.4 µg) isolated before induction with 0.5% L-arabinose ($t_0$); lane 3, XhoI digested plasmid-DNA (1.6 µg) isolated after 1 hour of induction with 0.5% L-arabinose ($t_1$); lane 4, XhoI digested plasmid-DNA (1.4 µg) isolated after 2 hours of induction with 0.5% L-arabinose ($t_2$).

FIG. 3 shows DNA preparation taken at various time points during the minicircle production process using parental plasmid pRBPS-IVR7_GFPCMV. In case of the time series shown in this figure the culture was induced at an $OD_{600}$ of 1,545. In lane one a preparation of the undigested parental plasmid was applied. The sample shown in lane two (1.4 μg DNA) was taken immediately before induction of the recombination process with 0.5% L-arabinose. Accordingly, digestion with XhoI results only in bands of 4722 bp and 2960 bp as expected for the parental plasmid.

The sample shown in lane 3 (1.6 μg DNA) was taken 1 hour after induction with 0.5% L-arabinose. Digestion with XhoI reveals almost exclusively one band with 2115 bp, which is the size of the resulting minicircle-DNA. Lane 4 (1.4 μg DNA) shows basically the same result for a sample taken after two hours of induction with 0.5% L-arabinose. Only trace amounts of residual parental plasmid-DNA can be observed in lane 3 and 4. A band with the size expected for miniplasmid-DNA (5567 bp) cannot be detected by restriction analysis and agarose gel electrophoresis in this example.

Figure 4:
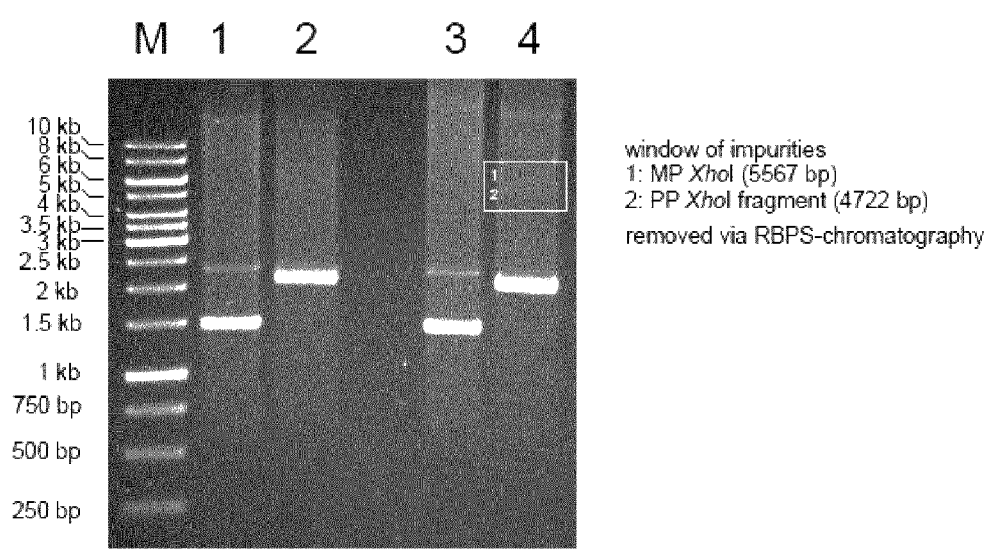
FIG. 4: Analysis of GFPCMV-minicircles derived from parental plasmid pRBPS7_IVR7_GFPCMV before (lane 3 and 4) and after (lane 1 and 2) RBPS chromatography. Digestion with XhoI resulted in a 4722 bp and a 2960 bp fragment in case of the parental plasmid (PP) and in the linearization of the miniplasmid (MP, 5567 bp) and the minicircle-DNA (2115 bp). Lane M, 1 kb DNA-ladder (GeneRuler, Fermentas); lane 1, minicircle-DNA derived from parental plasmid pRBPS7_IVR7_GFPCMV after RBPS chromatography undigested; lane 2, minicircle-DNA derived from parental plasmid pRBPS7_IVR7_GFPCMV after RBPS chromatography digested with XhoI; lane 3, minicircle-DNA derived from parental plasmid pRBPS7_IVR7_GFPCMV before RBPS chromatography undigested; lane 4, minicircle-DNA derived from parental plasmid pRBPS7_IVR7_GFPCMV before RBPS chromatography digested with XhoI.

In FIG. 4 preparations of minicircle-DNA derived from parental plasmid pRBPS-IVR7_GFPCM before and after RBPS-chromatography purification are shown. The culture for the production of the minicircle-DNA shown in this figure was induced at an $OD_{600}$ above 2. The lanes 3 and 4 show samples taken after two hours of induction. In lane 3 the undigested sample was applied on the agarose gel. In lane 4 the DNA preparation was digested with XhoI resulting the linearized minicircle band at 2115 bp and in additional weak bands at 5567 bp and 4722 bp resulting from residual miniplasmid and parental plasmid (marked by a frame). The DNA preparation shown in lane 3 and 4 was subjected to further purification with the herein described affinity chromatography system to remove these impurities. Lanes 1 and 2 show the sample after affinity chromatography. In lane 1 the undigested sample was applied. The sample shown in lane 2 has been digested with XhoI and subsequently subjected to agarose gelelectrophoresis. After affinity purification neither residual parental plasmid nor remaining miniplasmid-DNA can be detected.

The result shown in FIG. 3 clearly demonstrates the functionality of the system set-up as described herein. Prior to induction ($t_0$) only parental plasmid-DNA can be detected. After induction of the recombination process ($t_1$ and $t_2$) almost exclusively minicircle-DNA can be detected by agarose gelelectrophoresis. As the RBPS-IVR parental plasmid carries only one arabinose promoter which is exclusively responsible for the expression of the ParA resolvase, this outcome clearly shows that induction of ITev expression is triggered by the recombination event. The removal of the terminator sequences within the minicircle region allows expression of the endonuclease by the constitutive $lacI^q$ promoter. To detect residual impurities by ethidium bromid staining rather large amounts of DNA had to be applied for agarose gelelectrophoresis. In the case shown in FIG. 3 about 1.5 μg total DNA were applied to see the faint band representing the residual parental plasmid. This fact indicates the high efficiency of the involved processes and the high purity of the minicircle preparation shown in this Figure. Contaminations with parental plasmid and miniplasmid-DNA vary to some extend with process parameters like the $OD_{600}$ of the culture at the induction time-point. However, as demonstrated in FIG. 5 these remaining impurities can be removed by the herein described affinity chromatography.

REFERENCES

1. Jechlinger, W., *Optimization and delivery of plasmid DNA for vaccination.* Expert Rev Vaccines, 2006. 5(6): p. 803-25.
2. Darquet, A. M., et al., *A new DNA vehicle for nonviral gene delivery: supercoiled minicircle.* Gene Ther, 1997. 4(12): p. 1341-9.
3. Bigger, B. W., et al., *An araC-controlled bacterial cre expression system to produce DNA minicircle vectors for* nuclear and mitochondrial gene therapy. J Biol Chem, 2001. 276(25): p. 23018-27.
4. Chen, Z. Y., et al., *Minicircle DNA vectors devoid of bacterial DNA result in persistent and high-level transgene expression in vivo*. Mol Ther, 2003. 8(3): p. 495-500.
5. Jechlinger, W., et al., *Minicircle DNA immobilized in bacterial ghosts: in vivo production of safe non-viral DNA delivery vehicles*. J Mol Microbiol Biotechnol, 2004. 8(4): p. 222-31.
6. Mayrhofer, P., et al., *Minicircle-DNA production by site specific recombination and protein-DNA interaction chromatography*. J Gene Med, 2008. 10(11): p. 1253-69.
7. Chen, Z. Y., C. Y. He, and M. A. Kay, *Improved production and purification of minicircle DNA vector free of plasmid bacterial sequences and capable of persistent transgene expression in vivo*. Hum Gene Ther, 2005. 16(1): p. 126-31.
8. Kay, M. A., C. Y. He, and Z. Y. Chen, *A robust system for production of minicircle DNA vectors*. Nature biotechnology, 2010. 28(12): p. 1287-9.
9. Chen, H., et al., *Determination of the optimal aligned spacing between the Shine-Dalgarno sequence and the translation initiation codon of Escherichia coli mRNAs*. Nucleic Acids Res, 1994. 22(23): p. 4953-7.
10. Ringquist, S., et al., *Translation initiation in Escherichia coli: sequences within the ribosome-binding site*. Mol Microbiol, 1992. 6(9): p. 1219-29.
11. Schurr, T., E. Nadir, and H. Margalit, *Identification and characterization of E. coli ribosomal binding sites by free energy computation*. Nucleic Acids Res, 1993. 21(17): p. 4019-23.
12. Sadler, J. R., H. Sasmor, and J. L. Betz, *A perfectly symmetric lac operator binds the lac repressor very tightly*. Proc Natl Acad Sci USA, 1983. 80(22): p. 6785-9.
13. Cranenburgh, R. M., et al., *Escherichia coli strains that allow antibiotic-free plasmid selection and maintenance by repressor titration*. Nucleic Acids Res, 2001. 29(5): p. E26.
14. Mairhofer, J., et al., *A novel antibiotic free plasmid selection system: advances in safe and efficient DNA therapy*. Biotechnol J, 2008. 3(1): p. 83-9.

The invention claimed is:
1. A plasmid comprising the following units:
(a) an endonuclease restriction site,
(b) a promotorless endonuclease expression cassette,
(c) a promoter that is not operably linked to the endonuclease expression cassette,
(d) a sequence coding for an enzyme that catalyzes site-specific recombination,
(e) at least two recognition sequences for the enzyme catalyzing site-specific recombination,
(f) a sequence of interest between the at least two recognition sequences, and
(g) an element preventing the expression of the endonuclease positioned between the at least two recognition sequences,
wherein the promoter is operably linked to the endonuclease expression cassette after site-specific recombination occurs at the recognition sequences, and
wherein, upon expression of the sequence coding for the enzyme that catalyzes site-specific recombination, the plasmid is divided into (i) a minicircle comprising the sequence of interest and the element preventing the expression of the endonuclease and (ii) a miniplasmid comprising the endonuclease restriction site, the endonuclease expression cassette, the promoter, and the sequence coding for an enzyme that catalyzes site-specific recombination.

2. The plasmid according to claim 1, wherein the endonuclease is selected from the group consisting of I-TevI, I-CreI, I-DmoI, I-PpoI, I-SceI, and I-SceII.

3. The plasmid according to claim 1, wherein the plasmid further comprises at least one identification sequence.

4. The plasmid according to claim 3, wherein the identification sequence is a sequence which specifically binds to a protein to form a stable DNA-protein complex.

5. The plasmid according to claim 1, wherein the enzyme that catalyzes site-specific recombination is selected from the group consisting of ParA resolvase of plasmid RK2 or RP4, Φλ, integrase, ΦCh31 integrase, γδ resolvase, Hin recombinase, ΦP1 Cre, yeast 2 micron Flp, Tn3 resolvase, Tn21 resolvase, and XerCD.

6. The plasmid according to claim 1, wherein the recognition sequences for the enzyme that catalyzes site-specific recombination are selected from the group consisting of ParA resolution sites (res-sites), attB and attP for Φλ, integrase or ΦCh31 integrase, γδ res sites, hixL, hixR, lox sites, FRT sites, Tn3 res sites, Tn21 res sites, and cer sites.

7. The plasmid according to claim 1, wherein the element that prevents expression of the endonuclease is an operator and/or a transcription terminator.

8. The plasmid according to claim 1, wherein the plasmid comprises at least two elements that prevent expression of the endonuclease.

9. The plasmid according to claim 1, wherein the sequence of interest is a sequence coding for a product of value.

10. A method for providing a minicircle, comprising the following steps:
(a) transfecting a plasmid according claim 1 in an organism capable to replicate said plasmid,
(b) recombinating at the recognition sequences for the enzyme that catalyzes site-specific recombination, in order to obtain a minicircle comprising the sequence of interest and the element that prevents the expression of the recombinase and a miniplasmid comprising the endonuclease restriction site, the endonuclease expression cassette, the promoter and the sequence coding for an enzyme that catalyzes site-specific recombination,
(c) purifying the minicircle.

11. The method according to claim 10, wherein between step (b) and step (c) restricting the miniplasmid by means of the endonuclease is performed.

12. The method according to claim 10, wherein in step (c) the non-recombined plasmid and/or miniplasmid is/are immobilized on a solid support.

13. The method according to claim 10, wherein immobilizing is performed by means of a miniplasmid identification sequence, wherein the miniplasmid identification sequence is capable of specifically binding to a protein in order to form a stable DNA-protein complex.

14. The plasmid according to claim 3, wherein the identification sequence is a miniplasmid identification sequence.

15. The plasmid according to claim 4, wherein the identification sequence is a lac operator site which specifically binds to a LacI repressor protein.

16. The plasmid according to claim 1, wherein
the endonuclease restriction site is present on the miniplasmid after recombination,
the endonuclease is selected from the group consisting of I-TevI, I-CreI, I-DmoI, I-PpoI, I-SceI, and I-SceII, the plasmid further comprises at least one identification sequence, the identification sequence is a sequence which binds to a protein to form a stable DNA-protein complex, the enzyme that catalyzes site-specific recombination is selected from the group consisting of ParA resolvase of plasmid RK2 or RP4, Φλ, integrase, ΦCh31 integrase, γδ resolvase, Hin recombinase, ΦP1 Cre, yeast 2 micron Flp, Tn3 resolvase, Tn21 resolvase, and XerCD, the recognition sequences for the enzyme that catalyzes site-specific recombination are selected from the group consisting of ParA resolution sites (res-sites), attB and attP for Φλ, integrase or ΦCh31 integrase, γδ res sites, hixL, hixR, lox sites, FRT sites, Tn3 res sites, Tn21 res sites, and cer sites, the element that prevents expression of the endonuclease is an operator and/or a transcription terminator, and the plasmid comprises at least two elements that prevent expression of the endonuclease.

* * * * *

UNITED STATES PATENT AND TRADEMARK OFFICE
CERTIFICATE OF CORRECTION

PATENT NO. : 9,644,211 B2  Page 1 of 1
APPLICATION NO. : 14/785369
DATED : May 9, 2017
INVENTOR(S) : Mayrhofer It is certified that error appears in the above-identified patent and that said Letters Patent is hereby corrected as shown below:

In the Claims

Claim 15 at Column 24, Line 62, "Lad" should read "LacI"

Signed and Sealed this
First Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

| | | |
|---|---|---|
| PATENT NO. | : 9,644,211 B2 | Page 1 of 1 |
| APPLICATION NO. | : 14/785369 | |
| DATED | : May 9, 2017 | |
| INVENTOR(S) | : Mayrhofer | |

It is certified that error appears in the above-identified patent and that said Letters Patent is hereby corrected as shown below:

In the Claims

Claim 10 at Column 24, Line 42, "recombinase" should read "endonuclease"

Signed and Sealed this
Fourth Day of August, 2020

Andrei Iancu
*Director of the United States Patent and Trademark Office*